(12) United States Patent
Vatter

(10) Patent No.: US 7,404,966 B2
(45) Date of Patent: *Jul. 29, 2008

(54) TRANSFER-RESISTANT MAKEUP REMOVING COMPOSITIONS

(75) Inventor: Michael Lee Vatter, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 542 days.

This patent is subject to a terminal disclaimer.

(21) Appl. No.: 09/902,048

(22) Filed: Jul. 10, 2001

(65) Prior Publication Data

US 2002/0015684 A1 Feb. 7, 2002

Related U.S. Application Data

(60) Provisional application No. 60/217,120, filed on Jul. 10, 2000, provisional application No. 60/217,872, filed on Jul. 12, 2000.

(51) Int. Cl.
*A61K 8/02* (2006.01)
*A61K 9/14* (2006.01)
*A61K 9/50* (2006.01)

(52) U.S. Cl. ............... 424/401; 424/489; 424/502

(58) Field of Classification Search ............... 424/401, 424/63, 489, 502
See application file for complete search history.

(56) References Cited

U.S. PATENT DOCUMENTS

| | | | |
|---|---|---|---|
| 3,843,601 A | 10/1974 | Bruner | |
| 4,554,369 A | 11/1985 | Hill et al. | |
| 4,588,617 A | 5/1986 | Oka | |
| 4,720,353 A | 1/1988 | Bell | |
| 4,742,142 A | 5/1988 | Shimizu et al. | |
| 4,752,528 A | 6/1988 | Oka | |
| 4,761,454 A | 8/1988 | Oba et al. | |
| 4,780,145 A | 10/1988 | Mori et al. | |
| 4,970,252 A | 11/1990 | Sakuta et al. | |
| 4,980,167 A | 12/1990 | Harashima et al. | |
| 4,983,388 A | 1/1991 | Kuwata et al. | |
| 4,987,169 A | 1/1991 | Kuwata et al. | |
| 5,128,431 A | 7/1992 | Riding et al. | |
| 5,143,722 A | 9/1992 | Hollenberg et al. | |
| 5,220,033 A | 6/1993 | Kamei et al. | |
| 5,227,242 A * | 7/1993 | Walter et al. ............ 428/211 |
| 5,236,986 A | 8/1993 | Sakuta | |
| 5,266,321 A | 11/1993 | Shukuzaki et al. | |
| 5,280,019 A | 1/1994 | Kllimisch | |
| 5,330,747 A | 7/1994 | Krzysik | |
| 5,387,417 A | 2/1995 | Rentsch | |
| 5,399,342 A | 3/1995 | Krzysik | |
| 5,403,580 A | 4/1995 | Bujanowski et al. | |
| 5,412,004 A | 5/1995 | Tachibana et al. | |
| 5,512,272 A | 4/1996 | Krzysik | |
| 5,534,265 A * | 7/1996 | Fowler et al. ............ 424/489 |
| 5,599,533 A | 2/1997 | Stepniewski et al. | |
| 5,628,989 A | 5/1997 | Harashima et al. | |
| 5,654,362 A * | 8/1997 | Schulz et al. ............ 424/401 |
| 5,665,804 A | 9/1997 | Hill et al. | |
| 5,721,026 A | 2/1998 | Feder et al. | |
| 5,725,845 A | 3/1998 | Krog et al. | |
| 5,750,123 A | 5/1998 | Znaiden et al. | |
| 5,756,568 A | 5/1998 | Morita et al. | |
| 5,760,116 A | 6/1998 | Kilgour et al. | |
| 5,811,487 A | 9/1998 | Schulz, Jr. et al. | |
| 5,833,973 A | 11/1998 | Dobkowski et al. | |
| 5,837,793 A | 11/1998 | Harashima et al. | |
| 5,849,314 A | 12/1998 | Dobkowski et al. | |
| 5,853,711 A | 12/1998 | Nakamura et al. | |
| 5,853,741 A | 12/1998 | Znaiden et al. | |
| 5,854,336 A | 12/1998 | Divonne, Sr. et al. | |
| 5,859,069 A | 1/1999 | Yanagida | |
| 5,871,761 A | 2/1999 | Kuwata et al. | |
| 5,880,210 A | 3/1999 | Schulz, Jr. et al. | |
| 5,889,108 A | 3/1999 | Zhang | |
| 5,919,437 A | 7/1999 | Wilson et al. | |
| 5,919,468 A | 7/1999 | Bara | |
| 5,922,308 A | 7/1999 | Brewster et al. | |
| 5,929,164 A | 7/1999 | Zhang | |
| 5,143,722 A | 8/1999 | Hollenberg et al. | |
| 5,939,478 A | 8/1999 | Beck et al. | |
| 5,942,215 A | 8/1999 | Edwards et al. | |
| 5,945,471 A | 8/1999 | Morita et al. | |
| 5,948,855 A | 9/1999 | Lin et al. | |

(Continued)

FOREIGN PATENT DOCUMENTS

CA    1319306    6/1993

(Continued)

OTHER PUBLICATIONS

Richard J. Lewis, Sr., "Hawley's Condensed Chemical Dictionary-Thirteenth Edition", 1997, John Wiley & Sons (publisher), pp. 288 and 924.*

*Primary Examiner*—Shengjun Wang
(74) *Attorney, Agent, or Firm*—Laura L. Whitmer; Eric T. Addington; Angela K. Haughey

(57) ABSTRACT

The invention relates to a cleansing composition suitable for topical application to human skin, more particularly to an oil-based cleansing composition containing a silicone elastomer gelling agent for removal of make-up from the skin.

11 Claims, No Drawings

U.S. PATENT DOCUMENTS

| | | | |
|---|---|---|---|
| 5,969,035 A | 10/1999 | Meinhardt et al. | |
| 5,972,314 A | 10/1999 | Crotty et al. | |
| 5,977,280 A | 11/1999 | Kadlec et al. | |
| 5,985,807 A | 11/1999 | Auguste et al. | |
| 5,998,542 A | 12/1999 | Horne et al. | |
| 6,013,247 A | 1/2000 | Bara et al. | |
| 6,024,944 A | 2/2000 | Hansenne | |
| 6,027,738 A | 2/2000 | Stepniewski et al. | |
| 6,066,727 A | 5/2000 | Yamamoto et al. | |
| 6,071,503 A * | 6/2000 | Drechsler et al. | 424/63 |
| 6,074,672 A | 6/2000 | Dobkowski et al. | |
| 6,080,394 A | 6/2000 | Lin et al. | |
| 6,083,900 A | 7/2000 | Auguste et al. | |
| 6,103,250 A | 8/2000 | Brieva et al. | |
| 2001/0041768 A1 | 11/2001 | Lorant | |

FOREIGN PATENT DOCUMENTS

| | | |
|---|---|---|
| EP | 0 295886 A2 | 12/1988 |
| EP | 0 499398 A2 | 8/1992 |
| EP | 0 542498 A2 | 5/1993 |
| EP | 0 545002 A1 | 6/1993 |
| EP | 0 608 989 A2 | 8/1994 |
| EP | 0 796883 A2 | 9/1997 |
| EP | 0 829253 A2 | 3/1998 |
| EP | 0 848029 A2 | 6/1998 |
| EP | 0 850643 A1 | 7/1998 |
| EP | 0 855178 A2 | 7/1998 |
| EP | 0 882753 A1 | 9/1998 |
| EP | 0 908175 A1 | 4/1999 |
| EP | 0 917870 A1 | 5/1999 |
| EP | 0 934959 A1 | 8/1999 |
| EP | 0 958856 A1 | 11/1999 |
| EP | 0 972 512 A1 | 1/2000 |
| EP | 0 985402 A1 | 3/2000 |
| EP | 1 010715 A1 | 6/2000 |
| EP | 1 062944 A1 | 12/2000 |
| EP | 1 064930 A1 | 1/2001 |
| EP | 1 068852 A1 | 1/2001 |
| EP | 0 779322 B1 | 2/2001 |
| EP | 1 097968 A | 5/2001 |
| EP | 1095 959 A | 5/2001 |
| FR | 2 768 926 A1 | 4/1999 |
| FR | 2779440 A1 | 12/1999 |
| JP | SHO 61-194009 A | 8/1986 |
| JP | HEI 1-207354 A | 8/1989 |
| JP | HEI 4-017162 A | 3/1992 |
| JP | KOKAI 5-139929 A | 6/1993 |
| JP | 5-178733 A | 7/1993 |
| JP | 5-178734 | 7/1993 |
| JP | 6-72826 A | 3/1994 |
| JP | 7-258027 A | 10/1995 |
| JP | 7-277924 A | 10/1995 |
| JP | 8-259419 A | 10/1996 |
| JP | 8-295620 | 11/1996 |
| JP | 8-319215 A | 12/1996 |
| JP | 8-319218 A | 12/1996 |
| JP | 9-67233 A | 3/1997 |
| JP | 9-136813 A | 5/1997 |
| JP | 9-151126 A | 6/1997 |
| JP | 9-175939 A | 7/1997 |
| JP | 9-175940 A | 7/1997 |
| JP | 9-175990 A | 7/1997 |
| JP | 9-301825 A | 11/1997 |
| JP | 9-315936 A | 12/1997 |
| JP | 9-323917 A | 12/1997 |
| JP | 9-328409 A | 12/1997 |
| JP | 10-45536 A | 2/1998 |
| JP | 10-120525 A | 5/1998 |
| JP | 10-130120 A | 5/1998 |
| JP | 10-167925 A | 6/1998 |
| JP | 10-182354 A | 7/1998 |
| JP | 10-236917 A | 9/1998 |
| JP | 11-21227 A | 1/1999 |
| JP | 11-29436 A | 2/1999 |
| JP | 11-71236 A | 3/1999 |
| JP | 11-92335 A | 4/1999 |
| JP | 11-158036 A | 6/1999 |
| JP | 11-180847 A | 7/1999 |
| JP | 11-193214 A | 7/1999 |
| JP | 2000-7549 A | 1/2000 |
| JP | 2000-103717 A | 4/2000 |
| JP | 2000-226316 A | 8/2000 |
| WO | WO 96/18374 A1 | 6/1996 |
| WO | WO 97/44010 A1 | 11/1997 |
| WO | WO 98/00098 A1 | 1/1998 |
| WO | WO 98/00102 A1 | 1/1998 |
| WO | WO 98/00103 A1 | 1/1998 |
| WO | WO 98/00104 A1 | 1/1998 |
| WO | WO 98/00105 A1 | 1/1998 |
| WO | WO 98/42307 A1 | 10/1998 |
| WO | WO 99/00400 A1 | 1/1999 |
| WO | WO 99/13859 A1 | 3/1999 |
| WO | WO 99/22696 A1 | 5/1999 |
| WO | WO 99/43297 A2 | 9/1999 |
| WO | WO 99/51192 A2 | 10/1999 |
| WO | WO 99/63953 A1 | 12/1999 |
| WO | WO 00/21493 A1 | 4/2000 |
| WO | WO 00/61076 A1 | 10/2000 |
| WO | WO 00/61084 A1 | 10/2000 |
| WO | WO 00/72817 A1 | 12/2000 |
| WO | WO 01/12133 A2 | 2/2001 |

* cited by examiner

TRANSFER-RESISTANT MAKEUP REMOVING COMPOSITIONS

CROSS REFERENCE TO RELATED APPLICATION

This application claims the benefit of U.S. Provisional Application No. 60,217,120, filed Jul. 10, 2000 and U.S. Provisional Application No. 60,217,872, filed Jul. 12, 2000.

FIELD OF THE INVENTION

The invention relates to a cleansing composition suitable for topical application to human skin, more particularly to an oil-based cleansing composition containing a silicone elastomer gelling agent for removal of make-up from the skin.

BACKGROUND OF THE INVENTION

The topical application to human skin, in particular to the face of substances for cosmetic purposes, such as make-up, has since time immemorial been and still is, an art form employed particularly by women, as part of a daily or periodical ritual or routine to embellish or beautify their appearance in the eyes of the beholder and/or to enhance confidence, to enable them more readily to face each day. Topical application of make-up, particularly to exposed areas of the skin, can also provide some protection from the elements, such as the sun, the wind and the rain, where otherwise the skin damage or accelerated skin aging can occur.

Make-up, once applied to the skin, has conventionally only a limited life, and must be removed from time to time, in order to replenish it anew. To habitual make-up users, this is a daily or twice daily activity.

The removal of make-up, particularly so-called transfer resistant makeup, such as lipstick and mascara, presents a special problem since it is designed to adhere strongly to the skin and resist removal by aqueous solvents (e.g., as by perspiration or recreational water activities). Such transfer resistant products typically comprise a film former comprising gum or resin (e.g., silicone) in a volatile solvent.

Scrubbing of the skin to remove such make-up products can be successful, but damage to the underlying sensitive skin can result.

Oil based cleansing products such as 'cold cream' have been recommended for cleaning such make-up from the skin, but the resultant oil residue consisting of a mixture of solubilized make-up and excess oil cleanser is difficult to remove either by wiping off or by rinsing with water.

Surprisingly, it has been found that the use of silicone elastomer gels comprising at least one crosslinked organopolysiloxane elastomer in combination with an organic phase capable of dissolving a gum or resin material provide make-up removers which do not exhibit the above-mentioned disadvantages and which, after removal of the make-up, impart a smooth, silky soft feel to the skin. The compositions of the present invention also provide good make-up removal. The compositions of the present invention are especially useful in the removal of make-up compositions such as that disclosed in U.S. Pat. No. 6,019,962 to Rabe et al., which patent is herein incorporated by reference in its entirety.

Accordingly, an aspect of the present invention is to provide a method for removing transfer resistant make-up compositions which is both non-messy and imparts an improved after feel on the skin.

Another aspect of the present invention is to provide a method for removing gum and/or resin based transfer resistant make-up compositions by applying a safe and effective amount of a make-up removing composition comprising an organopolysiloxane elastomer and a solvent of specific solubility parameter.

SUMMARY OF INVENTION

The compositions of the present invention relate to a method for removing transfer resistant make-up compositions comprising the step of applying a safe and effective amount of a make-up removing composition comprising:

(i) from 0.1 to 30% of a crosslinked siloxane elastomer, preferably having a particle size of from above 10 to about 200 microns;

(ii) from 10 to 80% of a solvent having a solubility parameter of less than or equal to about 9 (or 9) $(cal./cm^3)^{1/2}$; and (iii) optionally, from about 0% to about 95% water preferably wherein the make-up contains at least about 10% by weight, more preferably at least 25% by weight, most preferably at least 35% by weight of a silicone gum and/or resin.

DETAILED DESCRIPTION OF THE INVENTION

As used herein, the term "make-up" refers to products that leave color on the face, including foundation, blacks and browns, i.e., mascara, concealers, eye liners, brow colors, eye shadows, blushers, lip colors, powders, solid emulsion compact, and so forth. The term "foundation" refers to liquid, creme, mousse, pancake, compact, concealer or like product created or reintroduced by cosmetic companies to even out the overall coloring of the skin. Foundation is manufactured to work better over moisturized and/or oiled skin.

The phrase "safe and effective amount" as used herein means an amount of a compound or composition sufficient to significantly induce a positive benefit, preferably a make-up removing benefit, including independently the benefits disclosed herein, but low enough to avoid serious side effects, i.e., to provide a reasonable benefit to risk ratio, within the scope of sound judgment of the skilled artisan.

The term "ambient conditions" as used herein refers to surrounding conditions under about one atmosphere of pressure, at about 50% relative humidity, and at about 25° C., unless otherwise specified.

As used herein the term "comprising" means that the composition can contain other ingredients which are compatible with the composition and which preferably do not substantially disrupt the compositions of the present invention. The term encompasses the terms "consisting of" and "consisting essentially of".

The phrase "transfer resistant", as used herein generally refers to cosmetic compositions which adhere extremely well to the skin and lips and are not readily blotted or transfered from the skin onto other surfaces such as glassware, silverware, clothing, etc. Similarly or alternatively, the phrase applies to cosmetic compositions which stay on the skin or lips for a substantial period of time before wearing and, hence do not require frequent reapplication.

The phrase "silicone gum and/or resin based", as used herein means that the cosmetic make-up composition to be removed or cleansed from the skin by the present invention contains sufficient silicone gum and/or resin to yield a total silicone gum and/or resin composition as a whole of least about 10% by weight, preferably at least about 20% by weight, most preferably at least about 30% by weight, up to an amount of about 40% by weight of the total composition, preferably in the range of about 30% to about 35%.

The phrases "silicone gum" and "silicone resin", as used herein, refer to those materials typically used in transfer resistant cosmetics and which are fully described in U.S. Pat. No. 6,071,503, issued Jun. 6, 2000, to Drechsler et al.; U.S. Pat. No. 6,019,962, issued Feb. 1, 2000, to Rabe et al.; and U.S. Pat. No. 5,849,310, issued Dec. 15, 1998, to Trinh et al.; each of which is herein incorporated by reference in its entirety.

Unless otherwise indicated, all percentages and ratios used herein are by weight of the total composition. All weight percentages, unless otherwise indicated, are on an actives weight basis. All measurements made are at 25° C., unless otherwise designated.

Crosslinked Siloxane Elastomer

An essential component of the present invention is a crosslinked organopolysiloxane elastomer. No specific restriction exists as to the type of curable organopolysiloxane composition which can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane; condensation-curing organopolysiloxane compositions which cure in the presence of an organotin compound or a titanate ester, by a condensation reaction between an hydroxyl-terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;

(B) an organopolysiloxane having at least 2 silicon-bonded hydrogen atoms in each molecule; and (C) a platinum-type catalyst.

With regard to the above, component (A) is the basic component of the silicone elastomer-generating organopolysiloxane, and curing proceeds by the addition reaction of this component with component (B) under catalysis by component (C). This component (A) must contain at least 2 silicon-bonded lower alkenyl groups in each molecule; an excellent cured product will not be obtained at few than two lower alkenyl groups because a network structure will not be formed. Said lower alkenyl groups are exemplified by vinyl, allyl, and propenyl. While the lower alkenyl groups can be present at any position in the molecular, their presence at the molecular terminals is preferred. The molecular structure of this component may be straight chain, branched straight chain, cyclic, or network, but a straight chain, possibly slightly branched, is preferred. The molecular weight of the component is not specifically restricted, and thus the viscosity may range from low viscosity liquids to very high viscosity gums. In order for the cured product to be obtained in the form of the rubbery elastomer, it is preferred that the viscosity at 25 degrees Centigrade be at least 100 centistokes. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers.

Component (B) is an organopolysiloxane having at least 2 silicon-bonded hydrogen atoms in each molecule and is a crosslinker for component (A). Curing proceeds by the addition reaction of the silicon-bonded hydrogen atoms in this component with the lower alkenyl groups in component (A) under catalysis by component (C). This component (B) must contain at least 2 silicon-bonded hydrogen atoms in each molecule in order to function as a crosslinker. Furthermore, the sum of the number of alkenyl groups in each molecule of component (A) and the number of silicon-bonded hydrogen atoms in each molecule of component (B) is to be at least 5. Values below 5 should be avoided because a network structure is then essentially not formed.

No specific restriction exists on the molecular structure of this component, and it may be any of straight chain, branch-containing straight chain, cyclic, etc. The molecular weight of this component is not specifically restricted, but it is preferred that the viscosity at 25 degrees Centigrade be 1 to 50,000 centistokes in order to obtain good miscibility with component (A). It is preferred that this component be added in a quantity such that the molar ratio between the total quantity of silicon-bonded hydrogen atoms in the instant component and the total quantity of all lower alkenyl groups in component (A) falls within the range of (1.5:1) to (20:1). It is difficult to obtain good curing properties when this molar ratio falls below 0.5:1. When (20:1) is exceeded, there is a tendency for the hardness to increase to high levels when the cured product is heated. Furthermore, when an organosiloxane containing substantial alkenyl is supplementarily added for the purpose of; for example, reinforcement, it is preferred that a supplemental addition of the instant SiH-containing component be made in a quantity offsetting these alkenyl groups. This component is concretely exemplified by trimethylsiloxy-terminated methylhydrogenpolysiloxanes, trimethylsiloxy-terminated dimethylsiloxane-methylhydrogensiloxane copolymers, and dimethylsiloxane-methylhydrogen-siloxane cyclic copolymers.

Component (C) is a catalyst of the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum. This component is added preferably at 0.1 to 1,000 weight parts, and more preferably at 1 to 100 weight parts, as platinum-type metal proper per 1,000,000 weight parts of the total quantity of components (A) plus (B). Other organic groups which may be bonded to silicon in the organopolysiloxane forming the basis for the above-described curable organopolysiloxane compositions are, for example, alkyl groups such as methyl, ethyl, propyl, butyl, and octyl; substituted alkyl groups such as 2-phenylethyl, 2-phenylpropyl, and 3,3,3-trifluoropropyl; aryl groups such as phenyl, tolyl, and xylyl; substituted aryl groups such as phenylethyl; and monovalent hydrocarbon groups substituted by, for example, the epoxy group, the carboxylate ester group, the mercapto group, etc.

Examples of the production of the organopolysiloxane elastomer powder are as follows: an organopolysiloxane composition as described above (additional-curable, condensation-curable, or peroxide-curable) is mixed with water in the presence of a surfactant (nonionic, anionic, cationic, or amphoteric), and, after mixing to homogeneity in a homomixer, colloid mill, homogenizer, propeller mixer, etc., this is cured by discharge into hot water (temperature at least 50 degrees Centigrade) and is then dried; the organopolysiloxane composition (addition-curable, condensation-curable, or peroxide-curable) is cured by spraying it directly into a heated current; the powder is obtained by curing a radiation-curable organopolysiloxane composition by spraying it under high energy radiation; the organopolysiloxane composition (addition-curable, condensation-curable, peroxide-curable) or high energy-curable organopolysiloxane composition is cured, the latter by high energy radiation, and the product is then pulverized using a known pulverizer such as, for example, a ball mill, atomizer, kneader, roll mill, etc., to thereby form the powder. Preferred organopolysiloxane compositions are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (Gransil™ line of materials). Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety. Preferably the elastomers of the present invention are cured under anhydrous conditions or in an anhydrous environment.

The cross-linked organopolysiloxane elastomers of the present invention are preferably further processed by subjecting them to a high shear (approximately 5,000 psi) treatment in the presence of a solvent for the siloxane elastomer via a Sonolator at less than 10 passes. Sonolation achieves a resultant composition with elastomer average particle size ranging from above 10 (or above about 10) microns to about 200 microns, preferably from about 20 to about 150 microns, more preferably from above 30 (or above about 30) to about 100 microns, most preferably from about 40 microns to about 95 microns, and, optimally, from above 50 microns to about 90 microns as measured by the Horiba LA-910 (described below). As used herein, the term "particle size" of the elastomer represents the elastomer particle size in its swelled state. By "swelled," as used herein, means that the elastomer particles have extended beyond their normal size and shape by virtue of their absorption of the solvent compound. Viscosity is best when ranging between above 20,000 (or above about 20,000) and about 6,000,000, preferably from about 30,000 to about 4,000,000, more preferably from about 40,000 to about 3,000,000, most preferably from about 60,000 to about 2,000,000, optimally about 70,000 to about 1,500,000 cps at 25° C. as measured by a Brookfield LV Viscometer (size 4 bar, 60 rpm, 0.3 sec.).

Without being limited by theory, the present inventors believe that compositions incorporating elastomer/solvent gels where the elastomer has an average particle size greater than 10 microns (or greater than about 10 microns) and/or viscosities greater than 20,000 cps.

Preferably, the cross-linked organopolysiloxane elastomers do not undergo recycled processing. Without being limited by theory, recycled processing produces broad particle size distributions comprising particles larger or smaller than that necessary to achieve the skin feel benefits of the present invention. Specifically, gel balls often result from silicone elastomer particles larger than 200 microns while elastomer particles smaller than 10 microns reduce skin feel and viscosity benefits. Such particle size distributions result from a failure to ensure that all of the elastomer particle materials experience the same shear throughout the process. Typically, with recycling, only a portion of the particles experience shear before these sheared particles are returned to the process starting point and combined with the remaining un-sheared particles. Similarly, the next cycle begins with only a portion of this particle mixture experiencing shear before the newly sheared mixture particles are returned to the process starting point and combined with the remaining un-sheared particle mixture. Importantly, even after considerable recycling, some of the particles never actually experience shear while others experience a high degree of shear. The result is a particle size range which encompasses particles both larger and smaller than those necessary to achieve the present invention.

In contrast, discrete pass processing, as alluded to above, ensures that all the particles experience shear as well as the same amount of shear with each run or pass. More specifically, no run or pass is completed until all the particles have experienced the same shear force. Consequently, the particle size distribution is narrower than that produced by "recycling" with respect to specific particle sizes. This results in a better balance between gel ball formation and viscosity as well as skin feel and viscosity.

Crosslinked organopolysiloxane elastomer can be of the non-emulsifying or emulsifying type or mixtures thereof. The term "non-emulsifying type," as used herein, defines crosslinked organopolysiloxane elastomer from which polyoxyalkylene units are absent. Emulsifying type crosslinked organopolysiloxane elastomer are described in U.S. Pat. No. 5,412,004 (issued May 2, 1995); U.S. Pat. No. 5,837,793 (issued Nov. 17, 1998); and U.S.Pat. No. 5,811,487 (issued Sep. 22, 1998), all of which are herein incorporated by reference in their entirety.

Preferably the cross-linked siloxane elastomer is non-spherical. Without being limited by theory, the present inventors believe that spherical particles fail to provide the rheology and film properties necessary to achieve the benefits of the present invention. Specifically, when forming the gel matrix or network, spherical particles do not swell to the extent and/or pack as tightly as non-spherical particles.

Amounts of the elastomer may range from about 0.1 to about 10%, optimally from about 1 to about 8%, most preferably from about 3 to about 6% by weight.

Solvent for the Crosslinked Siloxane Elastomer

The compositions of the present invention comprise a solvent for the crosslinked organopolysiloxane elastomer described hereinbefore. The solvent, when combined with the cross-linked organopolysiloxane elastomer particles, serves to suspend and swell the elastomer particles to provide an elastic, gel-like network or matrix. The solvent for the cross-linked siloxane elastomer is liquid under ambient conditions, and preferably has a low viscosity to provide for improved spreading on the skin.

Concentrations of the solvent in the cosmetic compositions of the present invention will vary primarily with the type and amount of solvent and the cross-linked siloxane elastomer employed. Preferred concentrations of the solvent are from about 10% to about 90%, preferably from about 20% to about 80%, more preferably from about 30% to about 70%, by weight of the composition.

The solvent for the cross-linked siloxane elastomer comprises one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The solvent for the cross-linked siloxane elastomer preferably has a solubility parameter of less than about 9 (or 9)(cal/cm$^3$)$^{0.5}$, more preferably from about 4 (or 4) to about 8.5 (or 8.5) (cal/cm$^3$)$^{0.5}$, most preferably from about 6 (6) to about 8 (or 8) (cal/cm$^3$)$^{0.5}$, optimally to about 6 (or 6) to about 7.5 (or 7.5)(cal/cm$^3$)$^{0.5}$. Solubility parameters for the liquid carriers or other materials, and means for determining such parameters, are well known in the chemical arts. A description of solubility parameters and means for determining them are described by C. D. Vaughan, "Solubility Effects in Product. Package, Penetration and Preservation"103 Cosmetics and Toiletries 47-69, October 1988; and C. D. Vaughan, "Using Solubility Parameters in Cosmetics Formulation", 36 J. Soc. Cosmetic Chemists 319-333, September/October, 1988.

Examples of suitable solvents include, but are not limited to, cyclomethicone (D5), dimethicone, cyclomethicone (D4), squalane, hexamethyldisiloxane, isocetyl stearate, squalene, polytetrafluoroethylene, perfluorodecalin, safflower oil, melene, almond oil, isopentane, avocado oil, arachidic acid, decyl oleate, C8-isoparaffin, diisopropyl ether, sperm oil, white mineral oil, tricosane, isodecyl oleate, chloesteryl oleate, peanut oil, hexane, linseed oil, octadecane, cyclohexane, dioctyl ether, eicosane, lanolin oil, petrolatum, behenic acid, diethyl ether, corn oil-refined, isostearyl neopentanoate, octyl palmitate, propyl fluoride, rice oil-so, tridecane, cottonseed oil, carbon dioxide, isopropyl linoleate, cod liver oil, erucic acid, cetyl octanoate, decene-1, dodecane, diethylhexyl adipate, isobutyl stearate, butyl myristate, butyl stearate, stearic acid, dioctyl maleate, isopropyl palmitate, dioctyl adipate, oleth-3, diethyl amine, linolenic acid, olive oil, palmitic acid, oleic acid, PEG-4 stearate, tridecyl neopentanoate, pentaerythritol tetraoleate, tocopheryl acetate, ethyl myristate, isopropyl myristate, turpentine (pinene), methyl oleate, cetyl acetate, methyl linoleate, isostearic acid, coconut oil, myristic acid, dibutylamine, octylamine, propylene glycol dipelargona, titanium isopropoxide, glycol distearate, glycol stearate, capric/caprylic triglyceride, isosteareth-2, PPG-2 myristyl ether, ricinoleic acid, staphylococcus aureus, glyceryl isostearate, glyceryl stearate (mono), laureth-4, limonene, propylene glycol laurate, octyl mercaptan, PEG-2 stearate, ethyl caprate, amyl acetate, glyceryl stearate se, diisopropyl adipate, lauric acid, polyethylene, diisopropyl amine, polyglyceryl-3 oleate, ethylene/vinyl acetate, ethyl caprylate, octyl acetate, octyl iodide, ethyl oleate, isopropylbenzene, sorbitain laurate, behenyl alcohol, isostearyl alcohol, lauraldehyde, ethyl caproate, cholesteryl propionate, isocetyl alcohol, decanone-2, octanal, trifluoroactylacetone, cholesteryl myristate, zinc stearate, citronellel, diethyl ketone, methyl isobutyl ketone, oxidized polyethylene, methyl heptyl ketone, myristyl lactate, capric acid, methyl caproate, arachidyl alcohol, dipropyl ketone, castor oil, polystyrene, stearyl alcohol, methyl hexyl ketone, octyl dodecanol, butyl acetate, cetyl alcohol, oleyl alcohol, propylene oxide and mixtures thereof.

Particularly preferred for us herein are cyclomethicone (D4 and/or D5), dimethicone, mineral oil, octyl palmitate, isostearic acid and mixtures thereof.

Water

The cosmetic compositions of the present invention optionally comprise water at from about 1% to about 95%, preferably from about 5% to about 90%, most preferably from about 10% to about 85%.

OPTIONAL INGREDIENTS

The compositions of the present invention can also contain optional ingredients to the extent that such optional ingredients do not adversely affect the performance of the present invention.

Skin Conditioning Agent

Optionally, the compositions of the present invention can further comprise a skin conditioning agent. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. When present, amounts of humectant may range anywhere from 1 to 50%, preferably from 10 to 40%, optimally from 25 to 35% by weight.

Exfoliants according to the present invention may be selected from C2-C30 alpha-hydroxycarboxylic acids, beta-hydroxycarboxylic acids and salts of these acids. Most preferred are glycolic, lactic and salicylic acids and their ammonium salts. Amounts of the exfoliants may range from 1 to 15%, preferably from 2 to 10% by weight.

A wide variety of C2-C30 alpha-hydroxycarboxylic acids may be employed. Suitable examples of which include:
  alpha-hydroxyethanoic acid
  alpha-hydroxypropanoic acid
  alpha-hydroxyhexanoic acid
  alpha-hydroxyoctanoic acid
  alpha-hydroxydecanoic acid
  alpha-hydroxydodecanoic acid
  alpha-hydroxytetradecanoic acid
  alpha-hydroxyhexadecanoic acid
  alpha-hydroxyoctadecanoic acid
  alpha-hydroxyeicosanoic acid
  alpha-hydroxydocosanoic acid
  alpha-hydroxyhexacosanoic acid, and
  alpha-hydroxyoctacosanoic acid When the conditioning agent is an emollient it may be selected from hydrocarbons, fatty acids, fatty alcohols and esters. Isononyl isononanoate is the most preferred hydrocarbon type of emollient conditioning agent. Other hydrocarbons that may be employed include mineral oil, polyolefins such as polydecene, and paraffins such as isohexadecane (e.g. Permethyl 99 Registered ™ and Permethyl 101 Registered ™).

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, safflower oil, cottonseed oil, corn oil, olive oil, cod liver oil, almond oil, avocado oil, palm oil, sesame oil, squalene, Kikui oil and soybean oil.

2. Acetoglyceride esters, such as acetylated monoglycerides.

3. Ethoxylated glycerides, such as ethoxylated glyceryl monostearate.

4. lAlkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Ether-esters such as fatty acid esters of ethoxylated fatty alcohols.

7. Polyhydric alcohol esters. Ethylene glycol mono and di-fatty acid esters, diethylene glycol mono-and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

8. Wax esters such as beeswax, spermaceti, myristyl myristate, stearyl stearate.

9. C1-C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 1:3 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Amounts of the skin conditioning agent may range from about 0% to 30%, preferably from about 1% to about 20%, optimally from about 1% to 10% by weight.

Solidifying Agent

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 1% to about 15%.

Suitable solidifying agents include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40-1.42, herein incorporated by reference.

Also useful herein are hydrophilic gelling agents such as the acrylic acid/ethyl acrylate copolymers and the carboxyvinyl polymers sold by the B.F. Goodrich Company under the trademark of Carbopol Registered ™ resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combination of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646, both of which are herein incorporated by reference in their entirety.

Additional examples of suitable gelling agents or gellants can be found in the Cosmetic Bench Reference, p. 1.27, herein incorporated by reference.

Further examples of suitable solidifying agents disclosed in the following references, all of which are incorporated by reference herein: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes", A. H. Warth, 2nd Edition, reprinted in 1960, Reinhold Publishing Corporation, pp 391-393 and 421; "The Petroleum Chemicals Industry", R. F. Goldstein and A. L. Waddeam, 3rd Edition (1967), E & F. N. Span Ltd., pp 33-40; "The Chemistry and Manufacture of Cosmetics", M. G. DeNavarre, 2nd edition (1970), Van Nostrand & Company, pp 354-376; and in "Encyclopedia of Chemical Technology:, Vol. 24, Kirk-Othmer, 3rd Edition (1979) pp 466-481; U.S. Pat. No. 4,126,679, Davy, et al., issued Nov. 21, 1978; European Patent Specification No. 117,070, May, published Aug. 29, 1984; U.S. Pat. No. 2,900,306, Slater, issued Aug. 18, 1959; U.S. Pat. No. 3,255,082, Barton, issued Jun. 7, 1966; U.S. Pat. No. 4,137, 306, Rubino, et al., issued Jan. 30, 1979; U.S. Pat. No. 4,154, 816, Roehl, et al., issued May 15, 1979; U.S. Pat. No. 4,226, 889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; European Patent Specification No. 24,365 Sampson, et al., published Mar. 4, 1981; and U.S. patent application Ser. No. 630,790, DiPietro, filed Jul. 13, 1984.

Preferably, the compositions of the present invention have a hardness value as measured using a TA-XT2i Texture Analyzer (described below) of up to about 25 gram-force, more preferably from about 0.5 to about 20 gram-force, most preferably from about 1 to about 15, optimally from about 1 to about 10 gram-force. Without being limited by theory, it is believed that compositions having stick hardness values above 25 gram-force tend to interfere with the formation of the film structure provided by the polysiloxane elastomer, thus, preventing the smoothness as well as improved uniformity and evenness of particle distribution within the film. This, in turn, negatively affects the sensory benefits of the cross-linked polysiloxane elastomer component.

Powder Fillers

The compositions of the present invention may also contain powder fillers. Powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, to El-Nokaly et al., issued Nov. 18, 1997, herein incorporated by reference in its entirety. These pigments and powders can be used independently or in combination.

Preferred organic powders/fillers include, but are not limited, to polymeric particles chosen from the methylsilsesquioxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyerene microspheres such as for example those sold by Dyno Particles under the name Dynospheres, ethylene acrylate copolymer sold by Kobo under the name FloBead EA209 and mixtures thereof.

Also useful herein are pigment and/or dye encapsulates such nanocolorants from BASF and multi-layer interference pigments such as Sicopearls from BASF.

It is preferred that the pigments/powders are surface treated to provide added stability of color and ease of formulation. Hydrophobically treated pigments are more preferred, because they may be more easily dispersed in the solvent/oil phase. In addition, it may be useful to treat the pigments with a material that is compatible with a silicone phase. Particularly useful hydrophobic pigment treatments for use in water-in-silicone emulsions include polysiloxane treatments such as those disclosed in U.S. Pat. No. 5,143,722, incorporated herein by reference in its entirety. Also preferred are pigment/powders having a primary average particle size of from about 10 nm to about 100,000 nm, more preferably from about 50 nm to about 5,000 nm, most preferably from about 100 nm to about 1000 nm. Mixtures of the same or different pigment/powder having different particle sizes are also useful herein (e.g., incorporating a TiO2 having a primary particle size of from about 100 nm to about 400 nm with a TiO2 having a primary particle size of from about 10 nm to about 50 nm).

Dispersants may also be used in conjunction with the colors and pigments of the present invention. Examples of suitable dispersants include, but are not limited to, those described in U.S. Pat. No. 5,688,493, herein incorporated by reference in its entirety.

Preservatives

Suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium Chloride, and methylbenzethonium chloride. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Emulsifiers

In addition to the emulsifying crosslinked siloxane elastomer, other emulsifiers or surfactants can be used herein. These emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986), each incorporated herein by reference in its entirety. Illustrative nonionic surfactants are alkoxylated compounds based on C10-C22 fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention. Anionic type emulsifiers or surfactants include fatty acid soaps, sodium lauryl sulphate, sodium lauryl ether sulphate, alkyl benzene sulphonate, mono- and di-alkyl acid phosphates and sodium fatty acyl isethionate. Amphoteric emulsifiers or surfactants include such materials as dialkylamine oxide and various types of betaines (such as cocamidopiopyl betaine).

Preferred for use herein are polyoxyalkylene copolymers also known as silicone polyethers. Polymers are described in detail in U.S. Pat. No. 4,268,499, which is incorporated herein by reference in its entirety. A particularly preferred polyoxyalkylene copolymer is known by its CTFA designation as dimethicones copolyol. A particularly preferred form of dimethicone copolyol is that supplied by Dow Corning as DC5225C.

The overall concentration of the emulsifier can be from 0% to about 10% of the formulation, preferably from 0.1% to about 5% and most preferably from about 0.1% to about 2%, by weight of the composition. Examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El-Nokaly et al.; and Examples of suitable moistures can be found in Cosmetic Bench Reference, pp. 1.22, 1.24-1.26 (1996), all of which are herein incorporated by reference in their entirety.

Aerated Compositions

Optionally and preferably, the compositions of the present invention are aerated. By "aerated" as used herein means the air is incorporated either by hand, mechanical mixing or by using any other form of conventional foaming or whipping instrument technology. Preferably the compositions of the present invention contain at least about 1%, preferably at least about 2%, optimally from about 3 to about 5% air.

Other Optional Ingredients

A variety of additional ingredients can be incorporated into the compositions of the present invention. Non-limiting examples of these additional ingredients include additional skin care actives such as peptides (e.g., Matrixyl [pentapetide derivative]), palmitoyl-oligopeptide, farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; sunscreens; anti-acne medicaments (resorcinol, salicylic acid, and the like); antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above mentioned vitamin $B_3$ compounds can be incorporated as re-crystallized crystals which remain in crystallized form in the composition or as partially solubilize crystals (i.e., some of the crystals are dissolved and some remain in crystalline form in the composition.).

Water-Insoluble Substrates

The compositions of the present invention can also be, optionally, incorporated into an insoluble substrate for application to the skin such as in the form of a treated wipe. Suitable water insoluble substrate materials and methods of manufacture are described in Riedel, "Non-woven Bonding Methods and Materials," *Non-woven World* (1987); *The Encyclopedia Americana*, vol. 11, pp. 147-153, vol. 21, pp. 376-383, and vol. 26, pp. 566-581 (1984); U.S. Pat. No. 3,485,786 to Evans, issued Dec. 23, 1969; U.S. Pat. No. 2,862,251, to Kalwarres, issued 1958; U.S. Pat. No. 3,025, 585, Kalwarres, issued 1967; U.S. Pat. No. 4,891,227, to Thaman et al., issued Jan. 2, 1990; and U.S. Pat. Nos. 4,891, 228 and 5,686,088 to Mitra et al., issued Nov. 11, 1997; U.S. Pat. No. 5,674,591; James et al; issued Oct. 7, 1997; all of which are herein incorporated by reference in their entirety.

Non-woven substrates made from synthetic materials useful in the present invention can also be obtained from a wide variety of commercial sources. Non-limiting examples of suitable nonwoven layer materials useful herein include PGI Miratec Herringbone, a patterned hydroentangled material containing about 30% rayon and 70% polyester, and having a basis weight of about 56 grams per square yard (gsy), available from PGI/Chicopee, Dayton N.J.; PGI Miratec Starburst, a patterned hydroentangled material containing about 30% rayon and 70% polyester, and having a basis weight of about 56 grams per square yard (gsy), available from PGI/Chicopee, Dayton N.J.; Novonet$^R$ 149-616, a thermo-bonded grid patterned material containing about 100% polypropylene, and having a basis weight of about 50 gsy, available from Veratec, Inc., Walpole, Mass.; Novonet$^R$ 149-801, a thermo-bonded grid patterned material containing about 69% rayon, about 25% polypropylene, and about 6% cotton, and having a basis weight of about 75 gsy, available from Veratec, Inc. Walpole, Mass.; Novonet$^R$ 149-191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex$^R$ 149-801, a nubbed, apertured hydroentangled material, containing about 100% polyester, and having a basis weight of about 70 gsy, available from Veratec, Inc. Walpole, Mass.; Keybak$^R$ 951V, a dry formed apertured material, containing about 75% rayon, about 25% acrylic fibers, and having a basis weight of about 43 gsy, available from PGI/Chicopee, Dayton, N.J.; Keybak$^R$ 1368, an apertured material, containing about 75% rayon, about 25% polyester, and having a basis weight of about 39 gsy, available from PGI/Chicopee, Dayton, N.J.; Duralace$^R$ 1236, an apertured, hydroentangled material, containing about 100% rayon, and having a basis weight from about 40 gsy to about 115 gsy, available from PGI/Chicopee, Dayton, N.J.; Duralace$^R$ 5904, an apertured, hydroentangled material, containing about 100% polyester, and having a basis weight from about 40 gsy to about 115 gsy, available from PGI/Chicopee, Dayton, N.J.; Sontara 8877, an apertured hydroentangled material, containing about 50% Nylon and about 50% Pulp, and having a basis weight of about 68 gsm, available from Dupont Chemical Corp.

Alternatively, the water insoluble substrate can be a polymeric mesh sponge as described in U.S. Pat. No. 5,650,384, incorporated by reference herein in its entirety. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

Preparation of the Substrate Material Impregnated with Cleansing Composition

Any method suitable for the application of aqueous or non-aqueous impregnates, including flood coating, spray coating or metered dosing, can be used to impregnate the fibrous webs herein with the cleansing compositions described herein. More specialized techniques, such as Meyer Rod, floating knife or doctor blade, which are typically used to impregnate liquids into absorbent sheets may also be used.

The composition should preferably comprise from about 100% to about 400%, preferably from about 100% to about 300% by weight of the absorbent sheet.

After coating, the sheets may be folded into stacks and packaged in any of the moisture and vapor impermeable packages known in the art.

The make-up removal compositions of the present invention are made via art recognized techniques for the various forms compositions.

Methods of Using the Cleansing Wipes

The make-up removal compositions and wipe of the present invention are useful for removing transfer resistant make-up compositions. Typically the wipe is used to apply the cleansing compositions to the area to be cleansed. The wipes herein can be used for personal cleansing when the use of cleansing products requiring water cannot be, or are inconvenient. Typical quantities of the present wipes useful for cleansing, range from about 1 to about 4 wipes per use, preferably from about 1 to about 2 wipes per use. Typical amounts of cleansing composition used range from about 4 mg/cm$^2$ to about 6 mg/cm$^2$, preferably about 5 mg/cm$^2$ of skin area to be cleansed.

Analytical Test Methods

Determination of Particle Size

Samples are prepared placing approximately 1 gram of the cross-linked elastomer (gel) in a small bottle with approximately 30 grams of a 1:1 isopropyl alcohol:dimethicone (DC 245) solution (IPA:DC245). The 1:1 IPA:DC245 solution is passed through a 0.2 μ syringe filter to remove foreign particulates (e.g., dust). The sample is then mixed (to disperse elastomer) using a Glass-Col Tissue Culture Rotator set at 70% for approximately 5 days.

The samples were, next, measured using a Horiba LA-910 equipped with a fraction cell holder and a magnetic stir bar. For a blank, a separate sample was prepared containing only the 30 grams 1:1 IPA:DC245. Before measurement, 10 ml aliquots of the prepared samples were placed in a small vial and allowed to settle for 30 minutes (to separate out large agglomerates). Stirring was used during measurement and the sampling time was set at 25 sec., the data were reported on a Volume basis using a relative refractive index of 1.06-0.00i. Samples are further diluted with 1:1 IPA:DC245 as necessary to achieve concentrations within the working range for the Horiba LA-910. More detailed instructions can be found in the Operator's Manuel for the Horiba LA 910, herein incorporated by reference. The process is additionally described in U.S. Pat. No. 5,998,542 and U.S. Pat. No. 5,929,162, both of which are herein incorporated by reference in their entirety Hardness Value Test The term "product hardness" as used herein is a reflection of how much force is required to move a rod a specified distance and at a controlled rate into a cosmetic composition under the following test conditions. Higher values represent harder product, and lower values represent softer product. These values are measured at 27° C., 15% relative humidity, using a TA-XT2i Texture Analyzer, available from Texture Technology Corp., Scarsdale, N.Y., U.S.A. The product hardness value as used herein represents the amount of force required to move a 16 mm long stainless steel rod having a 0.254 mm diameter through the composition for a distance of 12.2 mm at a rate of 0.85 mm/second. The rod is attached to the instrument by means of a suitable adapter (e.g., drill-type chuck). Other test parameters include: Pre-Test Speed of 0.85 mm/s, Post Test Speed of 1.70 mm/s, trigger distance of 0.1 mm. More detailed instructions can be found in the Operator's Manuel for the TA-XT2i, herein incorporated by reference.

The following examples will more fully illustrate the embodiments of this invention. All parts, percentages and proportions referred to herein and in the appended claims are by weight unless otherwise indicated.

EXAMPLES

The cosmetic products in the following examples illustrate specific embodiments of the cosmetic compositions of the present invention, but are not intended to be limiting thereof. Other modifications can be undertaken by the skilled artisan without departing from the spirit and scope of this invention. All exemplified compositions can be prepared by conventional formulation and mixing techniques. Component amounts are listed as weight percents and may exclude minor materials such as diluents, filler, and so forth. The listed formulations, therefore, comprise the listed components and any minor materials associated with such components.

Example 1

The following is an example of a make-up remover composition. The composition is formed by combining and mixing the ingredients of each row using conventional mixing technology, transferring the composition to an appropriate container or package, and then applying an appropriate amount of the composition on the skin to remove transfer-resistant cosmetics.

| Ingredient | Weight % |
| --- | --- |
| SFE 839 Silicone elastomer (5% elastomer in 95% D5) | 99.75 |
| Methylparaben | 0.15 |
| Propylparaben | 0.10 |

Example 2

The following is an example of a make-up remover composition providing sunscreen protection. The composition is formed by combining and mixing the ingredients of each row using conventional mixing technology, transferring the composition to an appropriate container or package, and then applying an appropriate amount of the composition on the skin to remove transfer-resistant cosmetics.

| Ingredient | Weight % |
| --- | --- |
| Micronized Titanium Dioxid | 2.0 |
| DC 9040 (12% elastomer in D5) | 94.9 |
| 5 cst dimethicone | 3.0 |
| Propylparaben | 0.1 |

Example 3

The following is an example of a make-up remover composition. The composition is formed by combining and mixing the ingredients of each row using conventional mixing technology, transferring the composition to an appropriate container or package, and then applying an appropriate amount of the composition on the skin to remove transfer-resistant cosmetics.

| Ingredient | Weight % |
| --- | --- |
| DC9040 (12% elastomer in D5) | 94.9 |
| Mineral oil | 5 |
| Propylparaben | 0.1 |

Example 4

The following is an example of a make-up remover composition. The composition is formed by combining and mixing the ingredients of each row using conventional mixing technology, transferring the composition to an appropriate container or package, and then applying an appropriate amount of the composition on the skin to remove transfer-resistant cosmetics.

| Ingredient | Weight % |
| --- | --- |
| KSG 16 (25% elastomer in dimethicone) | 98.9 |
| Propylparaben | 0.1 |
| Wax | 1.0 |

What is claimed is:

1. A method for removing transfer resistant make-up compositions comprising the step of applying a safe and effective amount of a make-up removing composition comprising:
    (i) from about 0.1 to about 30% of a non-spherical crosslinked siloxane elastomer said elastomer having a particle size of from above 10 to about 200 microns;
    (ii) from about 10 to about 80% of a solvent suitable for topical application to the skin having a solubility parameter of less than or equal to about 9 $(cal./cm^3)^{1/2}$;
    (iii) optionally, from about 0% to about 90% water and;
    (iv) an emulsifier
wherein the composition has a viscosity greater than about 20,000 cps.

2. The method of claim 1 wherein the transfer resistant make-up is silicone gum or resin based.

3. The method of claim 2 wherein the make-up removing composition further comprises a skin conditioning agent.

4. The method of claim 1 wherein the skin conditioning agent is selected from the group consisting of humectants, exfoliants, emollients and mixtures thereof.

5. The method of claim 4 wherein the skin conditioning agent is a humectant.

6. The method of claim 5 wherein the humectant is selected from the group consisting of propylene glycol, dipropylene glycol, polypropylene glycol, polyethylene glycol, sorbitol, hydroxypropyl sorbitol, hexylene glycol, glycerin, 1,3-butylene glycol, 1,2,6-hexanetriol, ethoxylated glycerin, propoxylated glycerin and mixtures thereof.

7. The method of claim 1 wherein the emulsifier is polyoxyalkylene copolymer.

8. The method of claim 7 wherein the polyoxyalkylene copolymer is dimetbicone copolyol.

9. The method of claim 1 wherein the crosslinked siloxane elastomer is a mixture of non-emulsifying and emulsifying crosslinked siloxane elastomers.

10. The method of claim 1 wherein makeup removing compositions further comprises an active selected from the group consisting of peptides, palmitoyl-oligopeptide, farnesol, bisabolal, phytantriol, glycerol, urea, guanidine, ascorbic acid, vitamin A, vitamin E, vitamin $B_3$, vitamin $B_5$, sunscreens, anti-acne medicaments; antioxidants, flavonoids, skin soothing and healing agents, chelators, sequestrants, opacifiers and mixtures thereof.

11. A cosmetic removing wipe, comprising:
A. one or more layers of water-insoluble substrate; and
B. a safe and effective amount of a make-up removing composition comprising;
  (i) from about 0.1 to about 30% of a non-spherical erosslinked siloxane elastomer said elastomer having a particle size of from above 10 to about 200 microns;
  (ii) from about 10 to about 80% of a solvent suitable for topical application to the skin having a solubility parameter of less than or equal to about 9 $(cal./cm^3)^{1/2}$;
  (iii) optionally, from about 0% to about 90% water and;
  (iv) an emulsifier
wherein the composition has a viscosity greater than about 20,000 cps.

* * * * *